(12) United States Patent
Sorenson

(10) Patent No.: US 7,912,652 B2
(45) Date of Patent: Mar. 22, 2011

(54) SYSTEM AND METHOD FOR MUTATION DETECTION AND IDENTIFICATION USING MIXED-BASE FREQUENCIES

(75) Inventor: Jon M. Sorenson, Oakland, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 475 days.

(21) Appl. No.: 10/293,960

(22) Filed: Nov. 13, 2002

(65) Prior Publication Data

US 2003/0194724 A1    Oct. 16, 2003

Related U.S. Application Data

(60) Provisional application No. 60/371,641, filed on Apr. 10, 2002.

(51) Int. Cl.
*G01N 33/48* (2006.01)
*C12Q 1/68* (2006.01)
*G06F 17/00* (2006.01)

(52) U.S. Cl. .................. 702/19; 435/6; 702/20; 700/90

(58) Field of Classification Search .................. None
See application file for complete search history.

(56) References Cited

U.S. PATENT DOCUMENTS 5,580,728 A  12/1996  Perlin
6,195,449 B1  2/2001  Bogden et al.

FOREIGN PATENT DOCUMENTS

WO    97/00972    1/1997

OTHER PUBLICATIONS

Phelps, R.S., "Efficient, Automatic Detection of Heterozygous Bases During Large-Scale DNA Sequence Screening," Dec. 1995, pp. 984-989, vol. 19, No. 6, *BioTechniques*.
PCT International Search Report from Application No. PCT/US03/09548, date of mailing Dec. 6, 2004.

*Primary Examiner* — Shubo (Joe) Zhou

(57) ABSTRACT

The present teachings disclose methods for evaluation of sequence information to characterize putative heterozygous indel mutations. The mutation analysis methods utilize sequence and trace information to identify mixed-base presence resulting from allelic differences. These methods may be applied to identify and resolve single nucleotide polymorphisms, insertions, deletions, and other mutational events.

49 Claims, 11 Drawing Sheets

MIXED BASE
NOMENCLATURE

R=G/A    H=A/C/T
Y=C/T    B=G/T/C
M=A/C    V=G/C/A
K=G/T    D=G/A/T
S=G/C    N=A/G/C/T
W=A/T

SEQUENCE LISTING

<160> NUMBER OF SEQ ID NOS: 19

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 ggaatgcc                                                                    8

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttatgtrcta tg                                                              12

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 ggaatscc                                                                    8

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
wmkakayacc mmwawawwwk wstywwawat wywsakr                                   37

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tagatacacc aataaattak wstywwawat wywsakr                                   37

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
wmkakayacc mmwawawwwt agtcttaaat attcaga        37

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (30)..(32)
<223> OTHER INFORMATION: a, c, t, g, unknown or other

<400> SEQUENCE: 7
cagtcaacat taataagtgc cncccnaaan nntgg        35

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other

<400> SEQUENCE: 8
ntanacaccc ctatatnnta gtcttaaata ttcaga        36

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 9
caanggkncc agggnattcc ccaggacaga aaggt        35

<210> SEQ ID NO 10
<211> LENGTH: 35

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other

<400> SEQUENCE: 10
aaagcgagca agagaatccc cgggnnnaaa gggna                               35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
trwkwkswkw kmakwtcaga mcagatactc ctgca                               35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
taatttgtga gcatttmaga acagawmmkm ywsym                               35

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggactcatca atctcctaag                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggactcatct atctcctaag                                                20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
```

```
ggactcatca aaaaaatctc ctaag                                          25

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 ggaatccc                                                              8

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 rymksw                                                                6

<210> SEQ ID NO 18
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 hvbd                                                                  4

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 19
rykmswhvbd n                                                         11
```

SYSTEM AND METHOD FOR MUTATION DETECTION AND IDENTIFICATION USING MIXED-BASE FREQUENCIES

CLAIM OF PRIORITY

This U.S. patent application claims priority to U.S. Provisional Patent Application No. 60/371,641, entitled "METHOD TO DETECT AND IDENTIFY HETEROZYGOUS INDEL MUTATIONS USING DIRECT SEQUENCING" filed Apr. 10, 2002 which is hereby incorporated by reference.

SEQUENCE LISTING

The instant application contains a Sequence Listing which has been submitted via EFS-Web and is hereby incorporated by reference in its entirety. Said ASCII copy, created on Apr. 2, 2010, is named 4839US.txt and is 5,776 bytes in size.

BACKGROUND

1. Field

The present teachings generally relate to nucleic acid analysis, and in various embodiments, to a system and methods for detecting and identifying heterozygous indel mutations.

2. Description of the Related Art

Allelic variations comprising differences in the genomic sequence between same-species organisms have be found to occur with relatively high frequency. For example, allelic variations referred to as single nucleotide polymorphisms (SNPs) are estimated to occur approximately one out of every three hundred basepairs, translating to an estimated total of over ten million SNPs in the human genome. Evaluating the frequency and distribution of allelic variations may be useful in identification of disease related loci and may serve as a diagnostic tool for determining genetic susceptibility to a variety of diseases including; hereditary thrombophilia, cystic fibrosis, and cancer. Existing methods for allelic variation identification generally necessitate the sequencing of large numbers of nucleotide fragments or strands generating vast amounts of data that must be sifted through to identify significant base differences. Using conventional data analysis approaches, difficulties often arise in identifying the presence and nature of a particular sequence variation. For example, differences between two alleles may result from insertion, deletion, or substitution of one or more bases. Identifying and distinguishing between these types of variations in an automated manner through computer-based analysis further presents problems in terms of accuracy and reliability. In this regard, there is a need for more robust analytical approaches that may be adapted for use with high-throughput sequencing methods to identify allelic variations with an improved degree of reliability and accuracy.

SUMMARY

In various embodiments, the present teachings describe methods for heterozygous indel mutation detection using direct sequencing information. By evaluating the number and distribution of mixed-bases within a target sequence characteristics of a mutational insertion or deletion, including location, size and composition, may be predicted. Additionally, evaluation of both forward and reverse sequence information in the locus of the mutation may improve the ability to distinguish mutational events from experimental noise and other systematic variations. The methods described herein may further be used in allelic differentiation and linkage disequilibrium analysis.

It is conceived that the methods described by the present teachings may be readily adapted to computer-based analysis applications and integrated into any of a number of sequencing and/or sample assembly software programs including the SEQSCAPE™ software analysis package (Applied Biosystems, CA). By applying these methods, additional functionalities may be obtained during sequence analysis including variant or mutation identification using direct sequencing information.

In one aspect, the invention comprises a method for identifying a putative mutation site within a target sequence comprising: (a) collecting sequence information for the target sequence comprising forward and reverse orientation sequence information; (b) scanning the forward orientation sequence information for a first mixed-base signature and the reverse orientation sequence information for a second mixed-base signature wherein the mixed-base signatures are derived from a selected locality of the target sequence; and (c) identifying the putative mutation site by comparison of the first mixed-base signature and the second mixed-base signature wherein a transition region characterized by an increase in mixed-base frequency is associated with the putative mutation site.

In another aspect, the invention comprises a method for performing allelic differentiation comprising: (a) collecting sequence information for a selected target sequence locus; (b) identifying a putative mutational event located within the selected target sequence locus by scanning the sequence information for a mixed-base signature; and (c) identifying the size of the putative mutational event by forming a plurality of shift hypotheses corresponding to predicted sizes for the putative mutational event that are resolved by performing a plurality of indel searches using the sequence information to identify one or more shift hypotheses that are supported by the mixed-base signature.

In still another aspect, the invention comprises a system for mutational analysis further comprising: A sequence collection module that receives sequence information for a target sequence comprising forward and reverse orientation sequence information; A scanning module that scans the sequence information to identify a first mixed-base signature associated with the forward orientation sequence information and a second mixed-base signature associated with the reverse orientation sequence information; and A signature correlation module that evaluates the first mixed-base signature relative to the second mixed-base signature to identify one or more putative mutation sites.

In a further aspect, the invention comprises a method for mutational analysis comprising: (a) receiving sequence information for a target sequence comprising forward and reverse orientation sequence information; (b) scanning the sequence information to identify a first mixed-base signature associated with the forward orientation sequence information and a second mixed-base signature associated with the reverse orientation sequence information; and (c) evaluating the first mixed-base signature relative to the second mixed-base signature to identify one or more putative mutation sites.

BRIEF DESCRIPTION OF THE DRAWINGS

These and other aspects, advantages, and novel features of the present teachings will become apparent upon reading the following detailed description and upon reference to the accompanying drawings. In the drawings, similar elements have similar reference numerals.

DESCRIPTION OF THE CERTAIN EMBODIMENTS

Figure 1C:
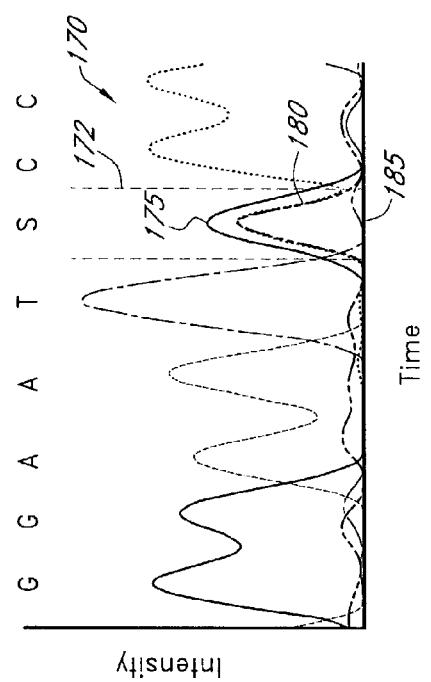
FIGS. 1A, B, C illustrate exemplary sequence traces associated with mixed-base analysis. (SEQ ID NO: 1) and (SEQ ID NO: 2) and (SEQ ID NO: 3)
Figure 1A:
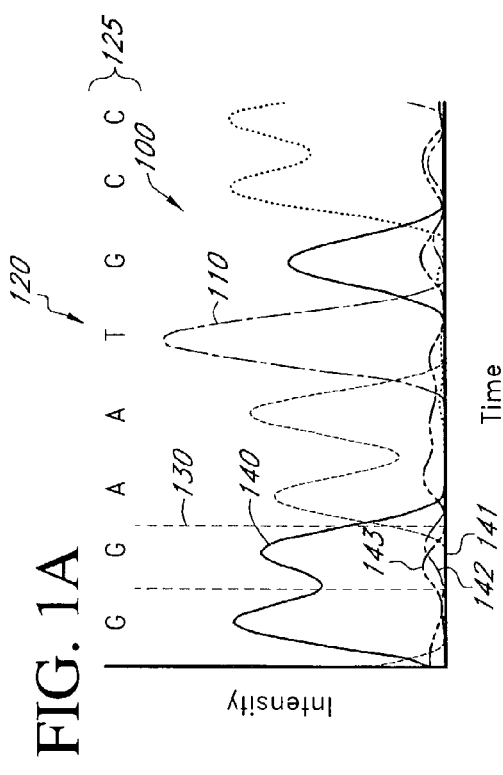

Reference will now be made to the drawings wherein like numerals refer to like elements throughout. As used herein, "target", "target polynucleotide", "target sequence" and "target base sequence" and the like refer to a specific polynucleotide sequence that may be subjected to any of a number of sequencing methods used to determine its composition (e.g. sequence). The target sequence may be composed of DNA, RNA, analogs thereof, or combinations thereof. The target may further be single-stranded or double-stranded. In sequencing processes, the target polynucleotide that forms a hybridization duplex with a sequencing primer may also be referred to as a "template". A template serves as a pattern for the synthesis of a complementary polynucleotide (Concise Dictionary of Biomedicine and Molecular Biology, (1996) CPL Scientific Publishing Services, CRC Press, Newbury, UK). The target sequence may be derived from any living or once living organism, including but not limited to prokaryote, eukaryote, plant, animal, and virus, as well as synthetic and/or recombinant target sequences.

Furthermore, as used herein, "sample assembly" and "assembly" refer to the reassembly or consensus analysis of smaller nucleotide sequences or fragments, arising from individually sequenced samples that may comprise at least a portion of a target sequence. By combining the information obtained from these fragments a "consensus sequence" may be identified that reflects the experimentally determined composition of the target sequence.

Nucleic acid sequencing, according to the present teachings, may be performed using enzymatic dideoxy chain-termination methods. Briefly described, these methods utilize oligonucleotide primers complementary to sites on a target sequence of interest. For each of the four possible bases (adenine, guanine, cytosine, thymine), a mixed population of labeled fragments complementary to a least a portion of the target sequence may be generated by enzymatic extension of the primer. The fragments contained in each population may then be separated by relative size using electrophoretic methods, such as gel or capillary electrophoresis, to generate a characteristic pattern or trace. Using knowledge of the terminal base composition of the oligonucleotide primers along with the trace information generated for each reaction allows for the sequence of the target to be deduced. For a more detailed description of sequencing methodologies the reader is referred to *DNA sequencing with chain-terminating inhibitors*, Sanger et. al., (1977) and *A system for rapid DNA sequencing with fluorescent chain-terminating dideoxynucleotides*, Prober et al., (1987).

The aforementioned sequencing methodology may be adapted to automated routines permitting rapid identification of target or sample sequence compositions. In an exemplary automated application, polynucleotide fragments corresponding to the target sequence are labeled with fluorescent dyes to distinguish and independently resolve each of the four bases in a combined reaction. In one aspect, a laser tuned to the excitation wavelength of each dye may be used in combination with a selected electrophoretic resolving/separation method to generate a distinguishable signal for each base. A detector may then transform the emission or intensity signal information into a sequencing trace representative of the composition of the sample sequence. The resulting data may then be subsequently processed by computerized methods to determine the sequence for the sample. For a more detailed description of a conventional automated sequencing system the reader is referred to *DNA Sequencing Analysis: Chemistry and Safety Guide* ABI PRISM 377 (Applied Biosystems, CA) and SEQSCAPE™ software documentation (Applied Biosystems, CA).

When performing comparative sequencing operations, two or more alleles corresponding to two or more alternative forms of a gene or nucleotide strand (for example arising from a chromosomal locus base difference) may be present in a single sequencing run. During electropherogram analysis, multiple alleles that differ at a particular sequence location may be identified by the presence of differing signals corresponding to each allele. In one aspect, the resulting signal profile may be referred to as a mixed-base signature.

One exemplary occurrence of allelic variation may be observed when two or more alleles differ with respect to a specific nucleotide position resulting in a polymorphism. For example, an exemplary 20-mer sequence "GGACTCATC(A)ATCTCCTAAG" (SEQ ID NO: 13) may represent a portion of a first nucleotide sequence that differs with respect to a second nucleotide sequence "GGACTCATC(T)ATCTCCTAAG" (SEQ ID NO: 14). The corresponding difference equating to a substitution froman "A" in the first sequence to a "T" in the second sequence exemplifies one type of allelic difference that may be observed during sequencing operations. Such a difference between sequences may further be observed in the electropherogram or sequencing trace at the location of the polymorphism wherein two or more distinguishable signals are observed in the same base location.

Alleles may also differ from one another by the insertion or deletion of one or more bases. For example a polymorphic insertion may be characterized by the exemplary 20-mer sequence "GGACTCATCAATCTCCTAAG" (SEQ ID NO: 13) representing a portion of a first nucleotide sequence that differs with respect to a second 25-mer nucleotide sequence "GGACTCATC(MAAA)AATCTCCTAAG" (SEQ ID NO: 15). Like single nucleotide polymorphisms, if alleles corresponding to an insertion or deletion are present in the biological source, they may be observable in an electropherogram trace in the form of a mixed-base signature. Allelic differences of this type may be generally referred to as heterozygous indel mutations HIM).

In the context of the present teachings, HIMs may further refer to sequence differences between two alleles or more than two alleles. Additionally, HIMs may comprise mutations that would lead to frameshifts if the nucleotide sequence was translated into a protein or amino acid sequence (e.g. an insertion or deletion that is not a multiple of three, corresponding to a shift in the translated codon sequence). HIMs may further comprise mutations that would not necessarily lead to frameshifts (therefore including insertions and deletions that are a multiple of three with no corresponding shift in the translated codon sequence). It is further conceived that the present teachings may also be applied in instances of single point mutations such as single nucleotide polymorphisms (SNPs) which may or may not lead to changes in the resultant translated protein or amino acid sequence.

FIG. 1I illustrates a portion of an exemplary electrophoretic or sequencing trace or chromatogram 100 for a sample polynucleotide that may be subjected to sequencing analysis in the aforementioned manner. The trace comprises fluorescence information translated into a series of peaks 110 for each of the bases, with each peak 110 representative of the detected signal or intensity for one of the four nucleotide bases (G, A, T, C). This information may be plotted as a function of time and the composition of the target sequence may be identified by determining the order of appearance of peaks 110 in the chromatogram 100. When evaluating each peak's intensity relative to other peaks in a similar localized region, a basecall 120 may be made which identifies the base that is predicted or calculated to be present at the selected position. Generally, each base position in the chromatograph corresponds to a single predominate peak that may be related to the base at that position within the sample sequence. For example, a base sequence 125 corresponding to 'GGAATGCC' (SEQ ID NO: 1) is identified by the trace 100.

During sequence analysis for any selected peak position, signals may be present which correspond to one or more of the bases. Thus, for a selected peak position 130, a plurality of signal components 140-143 may be observed which correspond to a G-signal component 140, an A-signal component 141, a T-signal component 142, and/or a C-signal component 143. The intensity of each detected base component is related to many factors and may include noise, sequencing reaction variations, and the presence of more than one allele for the target sequence. In one aspect, sequence analysis applications and/or software may be used to evaluate the trace information and make determinations as to what the likely base composition is for a selected peak position. In one aspect, such applications and/or software may further be used to evaluate signal intensities and discern between noise, experimental fluctuations, and actual base signals.

Figure 1B:
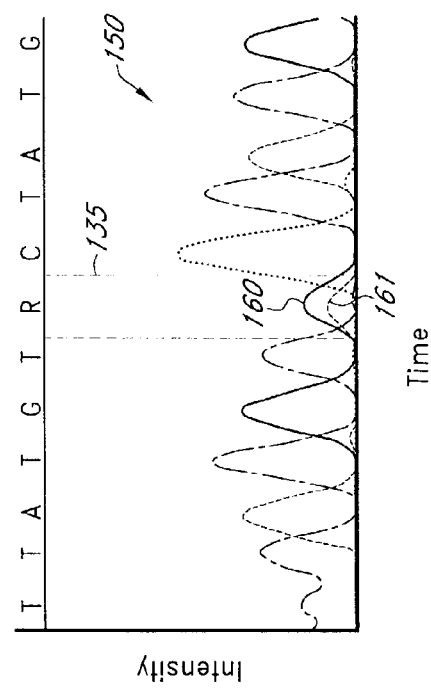

FIG. 1B illustrates an exemplary trace 150 having two or more identifiable peaks for a selected peak position 135 wherein a G-signal component 160 and an A-signal component 161 are present. The intensity of each signal component 160-161 may be such that the "true" basecall for this position within the sample sequence is not immediately obvious. In the illustrated embodiment, the basecall for the selected peak position 135 may be interpreted as either 'G' and/or 'A'. In the absence of additional data a value of 'R' might therefore be assigned to the selected peak position 135 indicating that the selected peak position 135 is occupied by more than a single base. According to the example described above, in instances where the base identity for a selected peak position 135 remains uncertain or cannot be readily resolved to a single base, one or more constituent bases may be identified to generate a compound or mixed-basecall wherein additional mixed-base nomenclature 165 is used to distinguish between various mixed-base compositions.

In FIG. 1C an exemplary chromatogram 170 having a candidate mixed-base 'S' at the selected peak position 172 may arise from two sample sequences 'GGAATGCC' (SEQ ID NO: 1) and 'GGAATCCC' (SEQ ID NO: 16). In this instance, each identified peak component 170, 175 may be representative of discrete bases, both of which may be present in the sample at the selected location. It will be appreciated that mixed-base presence as described above may result from allelic variations and/or genetic heterozygosity in the sample giving rise to two or more discrete sequences. A more detailed discussion of methodologies associated with mixed-base identification and analysis can be found in commonly-assigned U.S. patent application Ser. No. 10/279,746 entitled "A System and Method for Consensus-calling with Per-Base Quality Values for Sample Assembly", now U.S. Pat. No. 7,406,385 which is hereby incorporated by reference in its entirety.

In one aspect, the present teachings provide a means to detect and resolve heterozygous indel mutations through trace analysis using a mixed-base assessment approach. In various embodiments, the occurrence of one or more indel mutations within in a nucleotide sequence may be associated with the observance of a plurality of mixed-bases downstream of the mutational event. As will be described in greater detail hereinbelow, evaluation of the presence and distribution of mixed-bases in sequencing traces may be used to provide important insight as to the existence of indel mutations within a target sequence.

Figure 2:
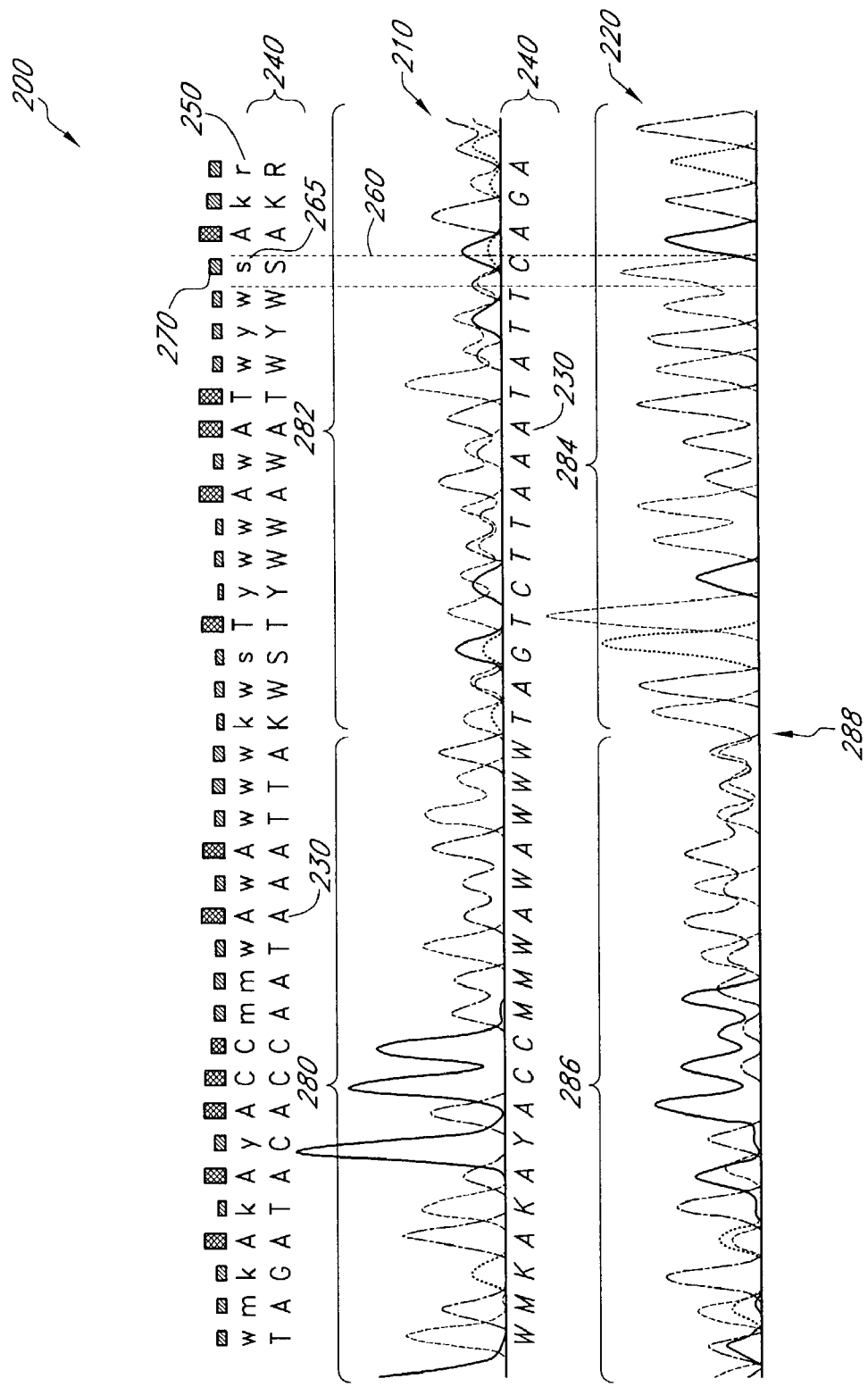
FIG. 2 illustrates exemplary sequence traces for a sample containing multiple alleles. (SEQ ID NO: 4) and (SEQ ID NO: 5) and (SEQ ID NO. 6)

FIG. 2 is a screenshot from SeqScape v1.1 showing the sequencing of a specimen containing two alleles differing by a deletion of TA at the center of the figure. The top strand is in the forward orientation and the bottom strand is in the reverse orientation (data from LUMC Netherlands, sequenced on 3700-POP6). Note that the SeqScape consensus calls correspond to one of the two alleles present and the application recognizes that the consensus sequence is of low quality.

Ideally one would like to display the presence of both sequences separated out for the user to see.

FIG. 2 illustrates exemplary trace data 200 for a nucleotide sequence containing two distinctive alleles. In one aspect, the presence of multiple alleles in a sequencing sample may be indicative of two or more nucleotide sequences that appear to differ with respect to at least a portion of their sequence. The trace data 200 comprises two sequencing traces or chromatograms 210, 220 for a sample polynucleotide that may be sequenced according to the labeling and amplification methodologies described above.

In the exemplary data, the forward trace 210 corresponds to sequence information obtained through sequencing of the nucleotide sample in a forward orientation while the reverse trace 220 corresponds to sequence information obtained through sequencing of the nucleotide sample in the reverse orientation. Each trace 210, 220 may further be associated with a plurality of basecalls 230 indicative of the predicted or calculated base composition for a selected peak position. In one aspect, each basecall 230 may further be associated with a quality value or confidence factor which may provide a means for assessing the relative level of accuracy associated with a particular basecall 230. As shown by way of illustration, in some instances the identified basecall is associated with an uppercase letter (e.g. A, T, C, G, etc) indicating that the consensus base may be different from the sample base, in which case the basecall in the sample may be overwritten. In one aspect, this manner of base identification may be used to distinguish differences in basecalls made by the consensus basecalling methods from that of the original basecall made prior to consensus analysis. Furthermore, a consensus basecall 250 may be generated by evaluating one or more of the basecalls associated with a selected peak position. Thus for the selected peak position 260, the individual basecalls 230 and associated quality values 270 for the forward and reverse traces 210, 220 may be evaluated to generate a corresponding consensus basecall 265 and consensus quality value 270.

According to the present teachings, mutational events and allelic differences may be identified by assessing the traces for mixed-base stretches. Furthermore, by comparing the forward and reverse orientations of the sample sequence, the location and type of mutational event or sequence difference may be identified. By way of example, when evaluating the forward orientation 210 for the exemplary sequencing data of a sample sequence, it may be observed that a first pure-base region 280 may exist wherein a substantial number of basecalls may be made with a high degree of confidence (e.g. high quality value) as there is generally a single predominant signal for each selected peak position. The pure-base region 280 may be flanked by a second mixed-base region 282 wherein one or more basecalls may possess a diminished degree of basecall confidence resulting from the presence of one or more mixed-base signals. Likewise, in assessing the reverse orientation 220, a second pure-base region 284 and a second mixed-base region 286 may be further identified in proximity to where these regions where observed in the forward orientation 210. In certain instances, the positioning of the pure-base region and the mixed-base region in the forward and reverse orientations appears to be substantially reversed or mirror images of one another.

When sequencing trace profiles having characteristics similar to those described above are encountered by conventional sequence analysis applications, there is often a significant reduction in the basecalling confidence in the mixed-base regions. This affects not only the basecalling accuracy for each strand or orientation but also affects the resultant consensus basecalls. In particular, conventional consensus basecalling may be susceptible to an increased frequency of basecalling error when confronted with stretches of mixed-bases. Oftentimes, additional sequencing reactions must be performed to increase the number of basecalls that are made before a consensus basecall is generated. Even with additional sequencing data, conventional methods generally fail to recognize and resolve the presence of mixed-base stretches when multiple alleles are present in the sample population.

A desirable feature of the present teachings is the ability to improve basecalling confidence by recognizing the presence of putative mutational events or multiple alleles in a sequencing trace having a high frequency of mixed bases. As will be described in greater detail hereinbelow, evaluation of sequence data in these regions of increased mixed-base frequency may be useful to resolve the composition of multiple alleles that may be present in the sequencing sample thereby improving overall efficiency in sequencing operations.

As an example of mutational analysis, by evaluating the traces 210, 220 in the forward and reverse directions in the above-described manner, an intersection point or region 288 may be identified where a mixed-base signal appears to the right of the intersection point 288 in the forward orientation and to the left of the intersection point 288 in the reverse orientation. It will be appreciated that the intersection point 288 may be indicative of a mutational event or allelic difference such as an insertion or deletion within the target sequence which results in two or more discrete sequences or alleles in the sample. Base differences between the two or more sequences contained in the same sample resulting in mixed base profiles are generally problematic for conventional sequence analysis approaches to resolve. However, by applying the methods described by the present teachings, these regions may be useful in determining the base composition for each allele present in the sample.

In addition to observing forward (or reverse) orientations for mixed-base stretches, further information about allelic differentiation and mutational events within these regions may be obtained by assessing the forward and reverse orientations 210, 220 in concert with one another. As will described in greater detail hereinbelow, evaluation of the sequencing data 100 in this manner may facilitate the determination of the length of the mutational event, as well as, its putative base composition.

One desirable feature of the above-described approach for mutational analysis and allelic differentiation using mixed-base signal assessment is that it may be applied to existing data sets and does not necessarily require new or additional sequencing reactions to be performed when sequencing a sample. This approach may further be used for a wide range of sequencing sample types, for example, to identify mutations in viral, bacterial, human, or other sample populations. In one aspect, the methodologies described herein are particularly suitable to adaptation to high-throughput direct sequencing projects that may be performed on a genomic scale. Using substantially the same sequencing data that is used to discern genomic sequence for a particular organism, additional useful information identifying regions of putative allelic differences and mutational events may be identified.

These methods may further be adapted for use in designing diagnostic assays to identify regions of allelic differences based on known relationships between a disease state and a mutational event. For example, a disease allele containing one or more frameshift mutations is the 35delG mutation of connexin 26 (gene GJB2). This mutation is thought to account for as much as 10-30% of sporadic non-syndromic deafness although the exact percentage may be population-specific. (*Med. J. Aust.*, 175, 191-194 (2001). and *Hum. Genet.*, 106, 50-57 (2000). A further mutation that may be observed in this region is the 167delT mutation. As will be described in greater detail hereinbelow, these disease-associated mutations may be associated with particular mixed-base sequence signatures. Therefore, performing mixed-base analysis in the aforementioned manner when sequencing selected genomic regions may desirably aid in identifying individuals who are at risk of a particular disease or diagnosing individuals who have contracted the disease.

Additional examples of allelic differences and mutational events that may be linked to significant biological or disease phenotypes and may further be identified by detection of mixed-base signatures according to the present invention include: (a) heteroplasmy in mtDNA resulting from indel mutations which often occur in repeated stretches such as the C stretch in the hyper-variable region 11. (*J Forensic Sci*, 46, 862-870 (2001)); (b) polymorphic markers in total color-blindness resulting from mutational events associated with CNGB3 (c) mutations in SLC7A7 resulting in lysinuric protein intolerance disorder and (d) mutations in ATP-binding cassette transporter 1 resulting in Tangier disease. From these examples, as well as others, it will be appreciated that identification of mutational events as described by the present teachings may play an important role in disease marker identification, susceptibility analysis, and diagnosis.

FIGS. 3 and 4 further detail the methodology by which indel mutations may be detected. It will be appreciated that these approaches may be adapted to detecting both single event mutations (e.g. a single insertion/deletion event) and multiple event mutations where more than one mutation may be present in the general locus of analysis. In various embodiments, a distinguishing feature of the present teachings is the ability to not only identify the presence of an allelic difference or mutational event but to also identify the type or nature of the mutation (e.g. an insertion, deletion, and/or substitution) and the size and/or sequence of the bases involved. As will be appreciated by one of skill in the art, in the case of a mixed allele, an insertion mutation can be identified as a deletion with respect to the other allele and vice versa. Thus, the definition of an insertion as compared to a deletion may be defined in terms of an available reference sequence with one not mutually exclusive of the other.

While the present teachings illustrate the principal of indel mutation identification using traces and basecalls for discrete sequences, it will be appreciated that automated methods may be developed that do not require a trace or basecall sequence to be displayed in such a manner and may instead be calculated using basecall (mixed-bases and pure bases) and quality value information. Furthermore, the size and composition of identified mutations may vary and need not necessarily conform to the properties illustrated in the exemplified traces. Additionally, the pure-base sequence may include a number of mixed-basecalls within this region and need not necessarily comprise strictly singly identifiable bases. In a similar manner the mixed-base region may include a number of non-mixed-bases and need not necessarily comprise strictly mixed-bases.

Figure 3A:
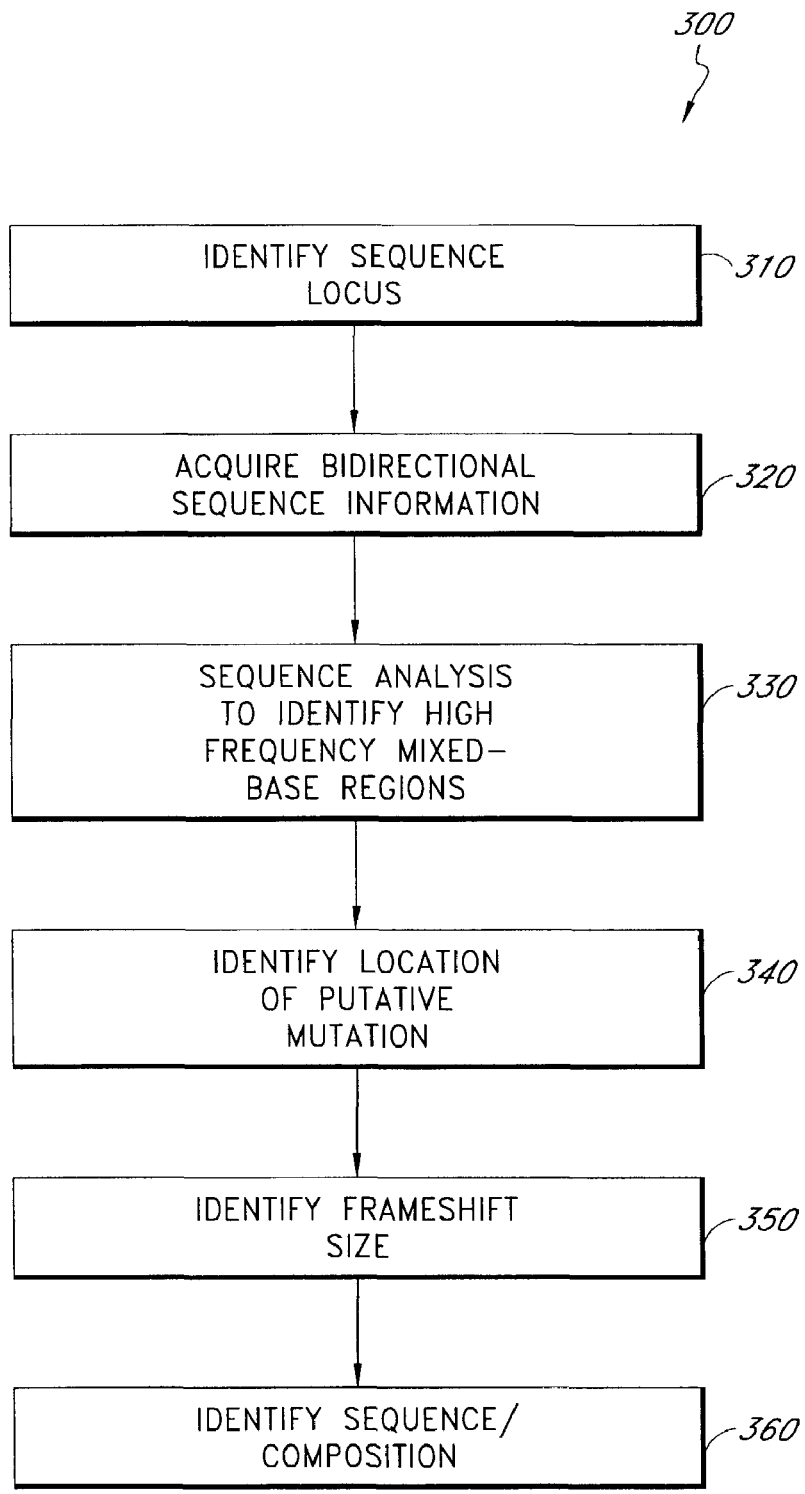
FIG. 3A illustrates a method for detection of heterozygous indel mutations.

FIG. 3A illustrates a method 300 for heterozygous indel mutation detection that applies a forward and reverse orientation assessment approach. The method commences in state 310 wherein the sequence locus to be evaluated is identified. The sequence locus is not limited with respect to size and may therefore represent a short nucleotide sequence or single gene of interest. Alternatively, the sequence locus may be much larger in scale (e.g. chromosomal or whole genome scale). Identification of the sequence locus therefore defines the scope of the mutational analysis for a given search and provides a means for determining if sufficient sequence information is available to span between the bounds of the locus. In instances of automated or high throughput sequencing operations, the sequence locus may be automatically identified by the sequencing instrumentation or software based upon the current sample undergoing processing.

Following sequence locus identification, the method 300 proceeds to a state 320 where bidirectional sequence information may be acquired for the sequence locus. As previously indicated, it may be desirable to collect both forward and reverse orientation sequence information which may include sequencing traces, basecall information, and/or quality value data. Furthermore, it may be desirable for the bidirectional sequence information to be complete with respect to the sequence locus; however, the methods described herein may be readily adapted to utilize incomplete sequence information in either the forward and/or reverse directions as needed or available.

In one aspect, the sequence information to be used in mutational analysis may be derived from existing databases or collections of sequence information such as public or private databases. Alternatively, the sequence information can be generated experimentally through direct sequencing of a sample in the appropriate locus and orientations. Furthermore, incomplete experimentally obtained sequence information can be supplemented with previously stored sequence information from existing databases or collections of sequence information and vice versa.

Once the bidirectional sequence information has been acquired, the method 300 proceeds to state 330 where sequence analysis is performed to identify regions within the sequence locus having a threshold frequency of mixed-bases. In one aspect, detection of the mixed-base frequency comprises evaluating the forward and reverse orientations of the sequence locus to detect any significant increases in the number of mixed-bases. As will be appreciated by one of skill in the art, during a typical sequencing run it is not uncommon for there to be at least some degree of mixed-base presence distributed throughout the sequence undergoing analysis. Mixed-bases resulting from experimental variations and artifacts may occur with random or sporadic frequency and generally may not sequentially track long stretches of the sequence. In certain instances, however, a stretch of mixed-bases may occur in a particular orientation of the sequence locus which may suggest the presence of a mutational event but is actually resultant from an experimental anomaly or other event.

Enzyme stutter is one such example of an experimental aberration that is desirably discerned from a mutational event. This phenomenon may occur during amplification of a sequence template containing one or more repetitive base sequences. As a result of incorrect pairing in the repeated sequences, one or more nucleotides may be added or deleted from the repeat region generating a mixed population containing a variable numbers or sizes of repeats. During trace analysis, enzyme stutter may result in stretches of mixed-bases that might otherwise resemble a mutational event due to the presence of the mixed population with variable numbers of repeats.

A distinguishing feature of the present teachings is that by using both forward and reverse sequence information anomalous or non-mutationally related mixed-base stretches including those generated as a result of enzyme stutter can be discerned by examining both the forward and reverse orientations. In various embodiments, bidirectional evaluation in this manner therefore provides a means to more accurately assess mutational events as sporadic or anomalous mixed-base stretches generally may not occur in both directions of the sequence locus in the same manner or with similar characteristics.

Figure 3B:
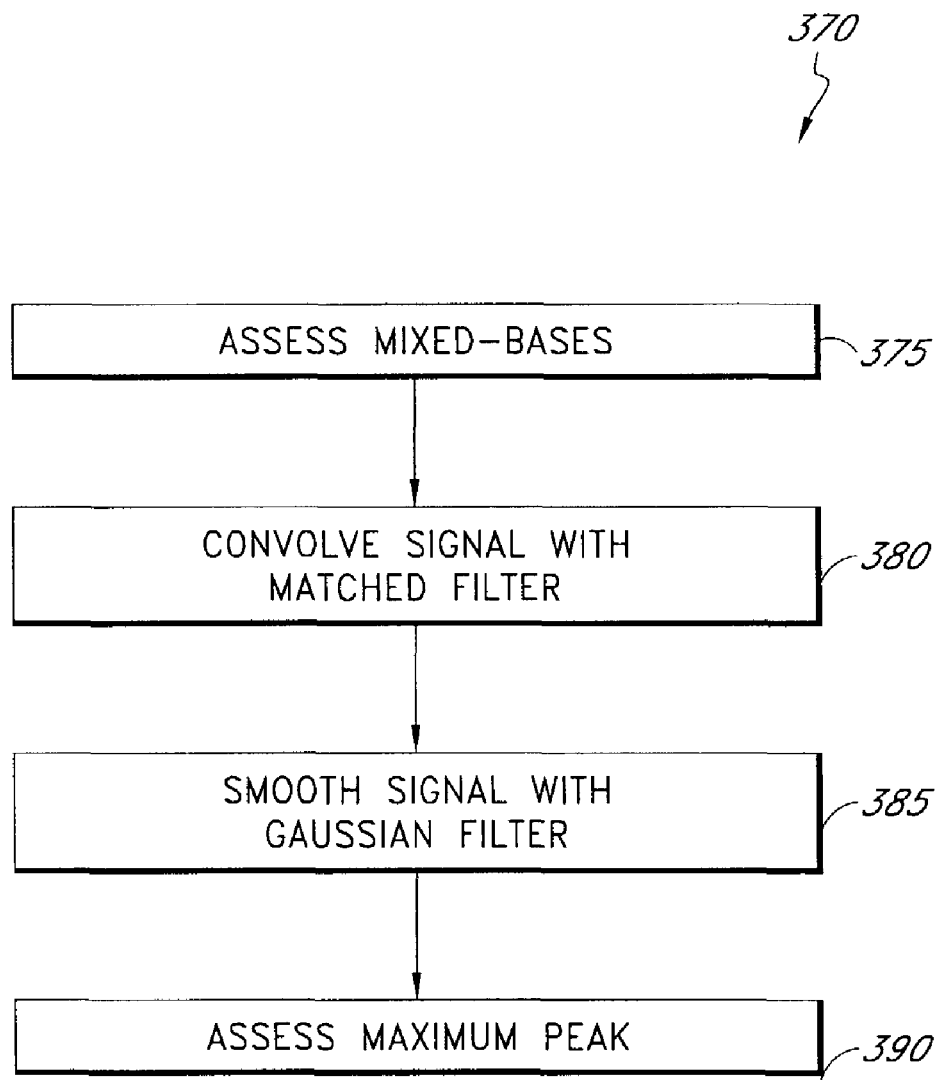
FIG. 3B illustrates a method for bidirectional assessment of mixed-base stretches.

As illustrated by way of example in FIG. 3B, bidirectional assessment of mixed-base stretches may be performed using a pattern detection approach 370. This method commences in state 375 with the evaluation of the number and positioning of mixed-bases in both forward and reverse orientations. Subsequently, the method 370 may proceed to a state 380 where a convolution assessment is performed using a matching filter to generate a convolution signal for each sequence orientation. Thereafter, in state 385 the signal(s) may be smoothened using a Gaussian step function which filters the generated signal(s). Finally, in state 390, a mixed-base frequency signal for each sequence orientation may be determined where the maximum peak in the smoothened signal is identified. In various embodiments, the smoothened signal from a first orientation may be convolved with other signals arising from opposing orientations from which the maximal peak assessment of state 390 is made. In one aspect, the bidirectional assessment of mixed-base stretches according to the aforementioned methodology may desirably improve automated detection and resolution of mutations present within the sequence locus. For a review of other signal processing approaches applying Gaussian smoothing operations and convolution methods, the reader is referred to (R O Duda, P E Hart, D G Stork. *Pattern Classification*. New York: John Wiley & Sons. 2001).

Upon identifying the number and positioning of mixed-bases in the sequence locus one or more mutational intersections or regions 288 are identified in state 340. Based on an increasing frequency of mixed-base presence, the intersection 288 serves as an indicator where a mutational event may occur within the sequence locus. For example, as previously illustrated in FIG. 2, the intersection 288 is identified by comparing mixed-base presence in the forward and reverse orientations to identify a region where one or more bases may be associated with different alleles.

After the location of a possible indel mutation has been discerned in state 340, the method 300 proceeds to state 350 where the size of the mutational event or indel is determined. In one aspect, this operation is performed using a shift hypotheses analysis approach discussed in detail with reference to FIGS. 4A, B. Briefly described, the shift hypothesis approach evaluates mixed-base stretches associated with a selected mutational intersection or region 288 to predict the size of the indel which may result from an insertion or deletion of one or more nucleotides in the differing alleles. Using this information, the method 300 may further predict the composition or sequence of the insertion or deletion in a subsequent state 360.

Once the aforementioned analysis method has been performed, relevant information pertaining to predicted heterozygous indel mutations may subsequently be stored and presented to the user. In one aspect, this analysis method and functionality may be readily integrated into an existing sequence processing package such as the SEQSCAPE™ software application for variant identification (Applied Biosystems). Additionally, predicted mutational regions may be presented to the user in an easy to interpret format including a graphical presentation format or in a textual format listing its location, size, and/or composition.

Figures 4A, 4B:
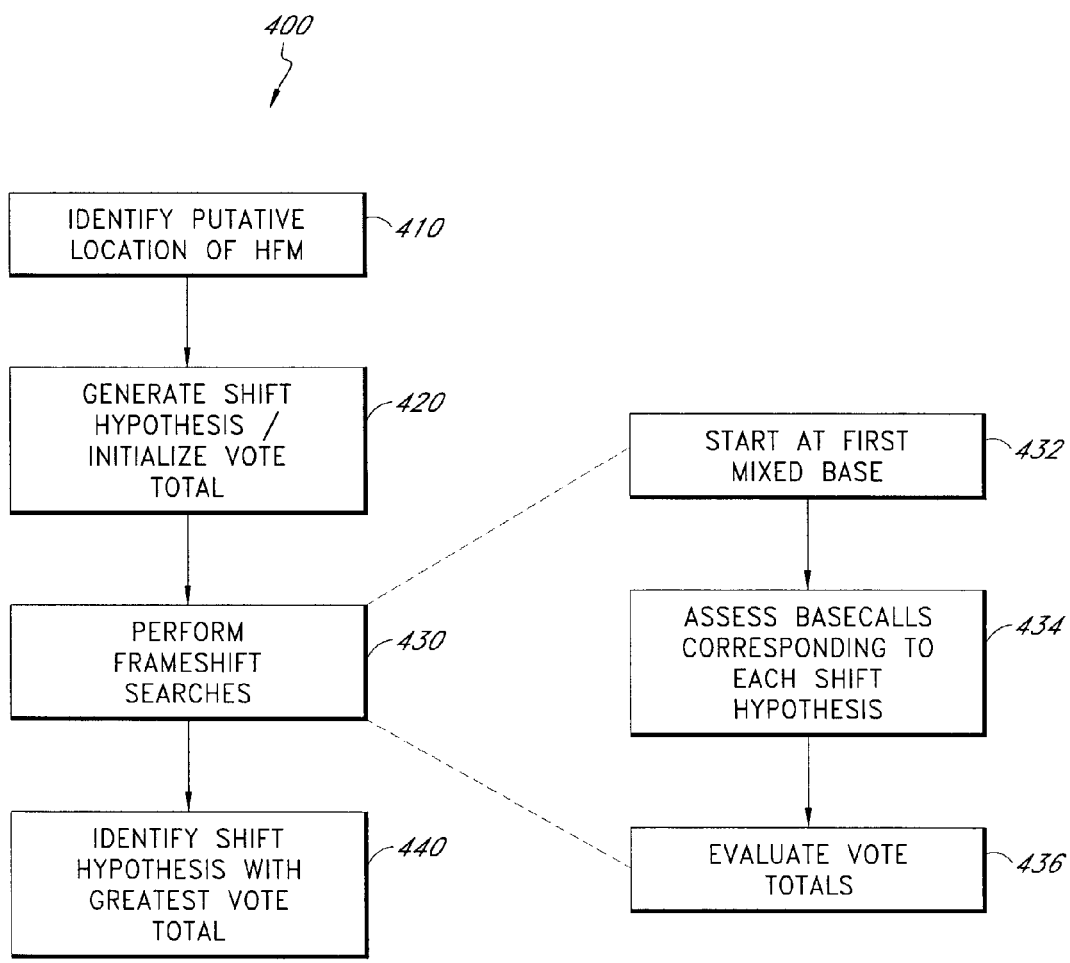
FIG. 4A illustrates a method for size determination of heterozygous indel mutations.
FIG. 4B illustrates a shift resolution process that may be used in size determination of heterozygous indel mutations.

FIGS. 4A, B illustrate an exemplary method 400 for size determination of putative heterozygous indel mutations. In one aspect, the method 400 commences in state 410 with the identification of the putative location of the mutation. This information is typically identified from trace evaluation using forward and reverse orientational analysis as previously described to identify a position where mixed-base stretches generally occur in substantially opposing orientations in the forward and reverse directions.

Figure 5:
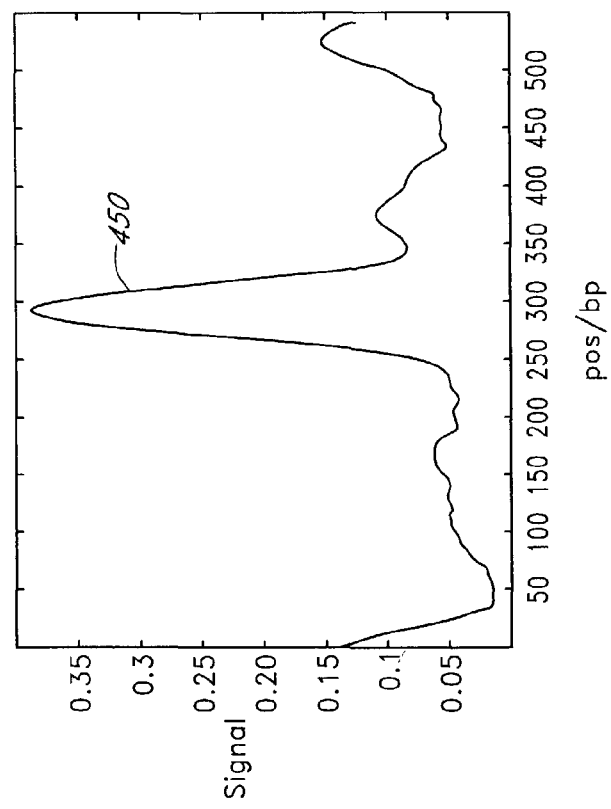
FIG. 5 illustrates a graphical representation of exemplary results obtained from the method for detection of heterozygous indel mutations.

As illustrated by way of a computational function coded in MATLAB® instructions shown in Appendix A, the location of the mutation may be resolved by scanning the sample assemblies for a substantial increase in the mixed-base frequency. An exemplary operation of this function is illustrated in FIG. 5 with the result shown in graphical form. When analyzing a sample sequence having a putative mutation, a plot of the signal strength versus the base position may be used to identify increases in mixed-base frequency graphed as a function of signal intensity for each location in the sample sequence. Typically, such a graph will give rise to one or more peaks, indicating regions within the sample sequence where stretches of mixed-bases occur. From this information, the maximal signal intensity corresponding to the largest peak may be associated with the location of the mutational event. In the exemplary sequence shown in FIG. 5, a mutational insertion 450 is shown to occur at a location of approximately 300 basepairs where a strong increase in mixed-base frequency is observed.

Referring again to FIG. 4A, once the putative location of the mutation has been identified in step 410, the method proceeds to step 420 where a plurality of shift hypotheses are formed. Each shift hypothesis corresponds to a predicted size of the mutational event (whether it be an insertion or deletion). In one aspect, the quantity of shift hypotheses may be based on a size range of approximately 1 to 50 nucleotides or more. Each shift hypothesis may further be associated with a value corresponding to vote total which represents a quantification of the likelihood that a particular shift hypothesis fits the mixed-base profile compared to that of other shift hypothesis. In various embodiments, each vote total may be initially set to a value of zero and is subsequently incremented or decremented by a selected value(s) based on the composition of nucleotides in the associated shift hypothesis.

In state 430, each shift hypothesis is resolved either incrementally or in parallel by applying a shift resolution function. An exemplary instructional function coded in MATLAB instructions for performing shift resolution is shown in Appendix B. According to this function, shift resolution commences with the first identified mixed-base contained in the shift hypothesis (FIG. 4B, state 432). In one aspect, the function may proceed incrementally for a selected number of basecalls and perform vote totaling as will be described in greater detail hereinbelow. While the number of basecalls searched within each shift hypothesis is variable, a selected search number between approximately 20-100 has been found to operate well in conjunction with the aforementioned shift resolution function.

In one aspect, the shift resolution operation (FIG. 4B, state 434), comprises a search for indels starting at approximately the first mixed-base adjacent to the putative heterozygous indel mutation location for sequences in the forward orientation. In a similar manner, a search for indels starting at approximately the first mixed-base adjacent to the putative mutation location is performed for sequences in the reverse (opposing) orientation. For each shift hypothesis "k" to be evaluated, a check is performed to determine if the basecall "k" bases away supports the hypothesis. In one aspect a supported shift hypothesis may be representative of an expected signal intensity or detected base occurring at a selected location within the trace. If the basecall at the selected location supports the hypothesis then the vote total may be incremented by a selected value. Alternatively, if the basecall does not support the hypothesis then the vote total may be decremented. In one aspect, supported basecalls result in an incrementing of the vote total by one whereas non-supported basecalls result in a decrementing of the vote total by two. Upon completion of the shift hypothesis analysis, the vote totals for each shift hypothesis are evaluated (FIG. 4B, state 436). In one aspect, the hypothesis with the most votes is identified as the best approximation for the size of the indel.

Figure 6:
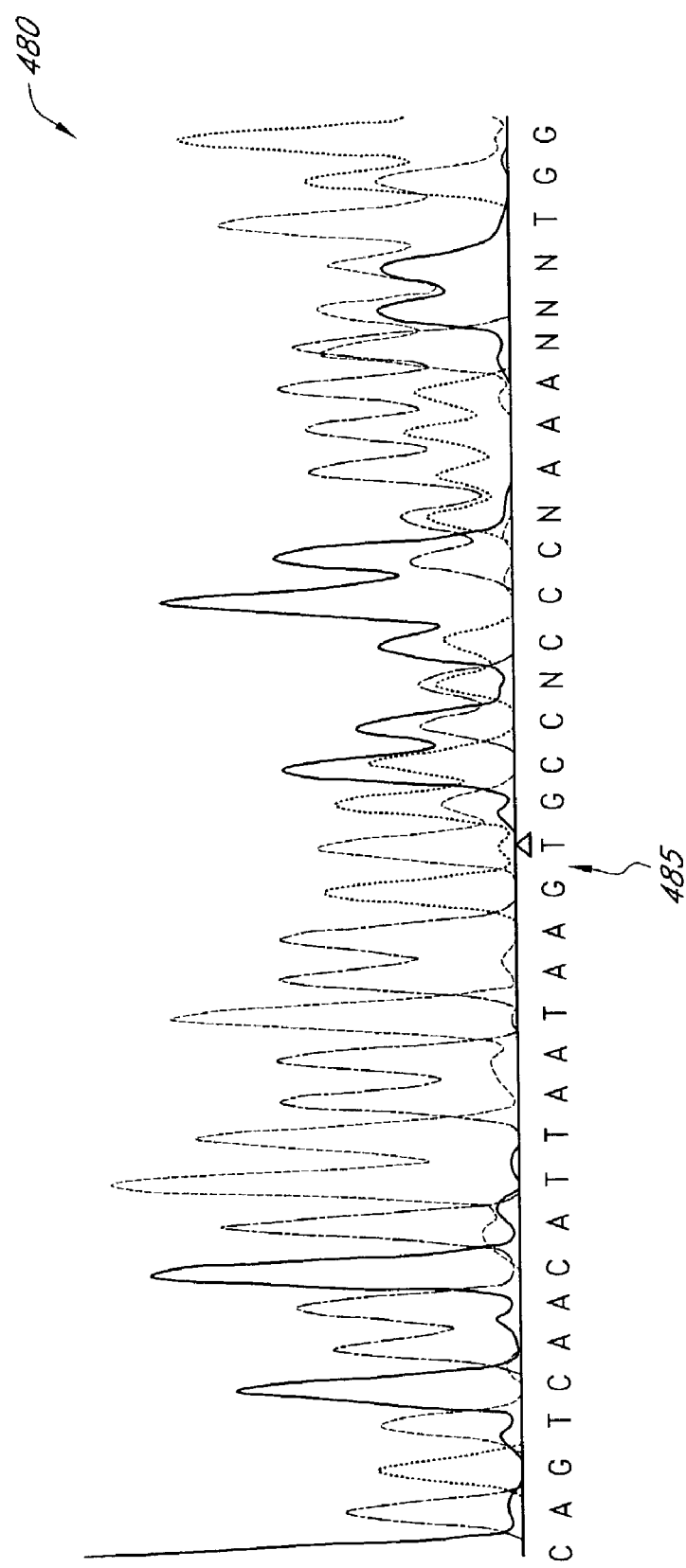
FIG. 6 illustrates a trace analysis of exemplary results obtained from the mutation size determination process. (SEQ ID NO: 7)

FIG. 6 illustrates the operation of the size determination function as it relates to an exemplary trace 480 for a sample sequence in the forward orientation having a single basepair insertion. An application of the size determination function starts at the peak one basepair to the right of the identified mutational start location 485 (indicated by the triangle). This peak corresponds to a mixed-base and from this location the function scans to the right to identify any shift hypothesis for which there is support. As demonstrated by the trace, there is support for shift hypotheses of 1, 3, 4, 7, 8, 9, 10, 11, 12, 13, 14, or 15 basepairs to the right of the mutational start location 485. It will be appreciated by one of skill in the art that other shift hypothesis may be possible that extend beyond the limits of the window of the exemplified trace. Generally, as the function proceeds further away from the mutational start location 485, in this case, extending more bases to the right there is a rapid narrowing of possible shift hypotheses.

To further exemplify how the shift hypothesis support approach operates, a series of sample analysis are described below based on the trace 480 using an incremental comparison of supported and non-supported hypothesis. According to the mutational start location 485 identified in the trace, starting at the next base, there is support for a shift hypothesis of 1, 2, 3, 4, 5, 6, 7, 8, 9, 11, 12, 14, and 15. Similarly, starting at the subsequent base, there is support for a shift hypothesis of 1, 2, 3, 4, 5, 6, 7, 8, 9, 10, and 11. Likewise, starting at the next base, there is support for a shift hypothesis of 1, 3, 4, 5, 6, 7, 8, 9, and 10. Based on the identified shift hypothesis for each base position, a comparison of the obtained information may be made to arrive at the calculated size for the indel sequence. It will be appreciated that the number of shift hypothesis and number of bases that are scanned may vary from one sequence to the next and therefore is not limited to the number and size shown in the example above.

Figure 7:
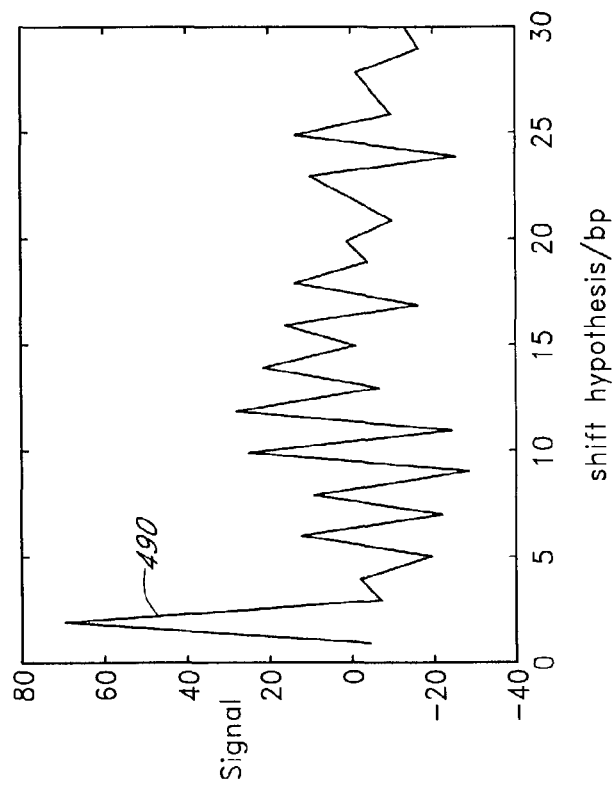
FIG. 7 illustrates a graphical representation of shift resolution for a first indel mutation.

FIG. 7 demonstrates the results of the voting totals obtained from application of the mutational length identification function using an exemplary sample sequence. By evaluating the vote total for each shift hypothesis relative to one another the shift hypothesis with the greatest score may be associated with the length of the insertion or deletion. In the case of the illustration, a strong signal intensity 490 appears for the 2 basepair shift hypothesis supporting a predicted insertion length of 2 basepairs.

Figure 8:
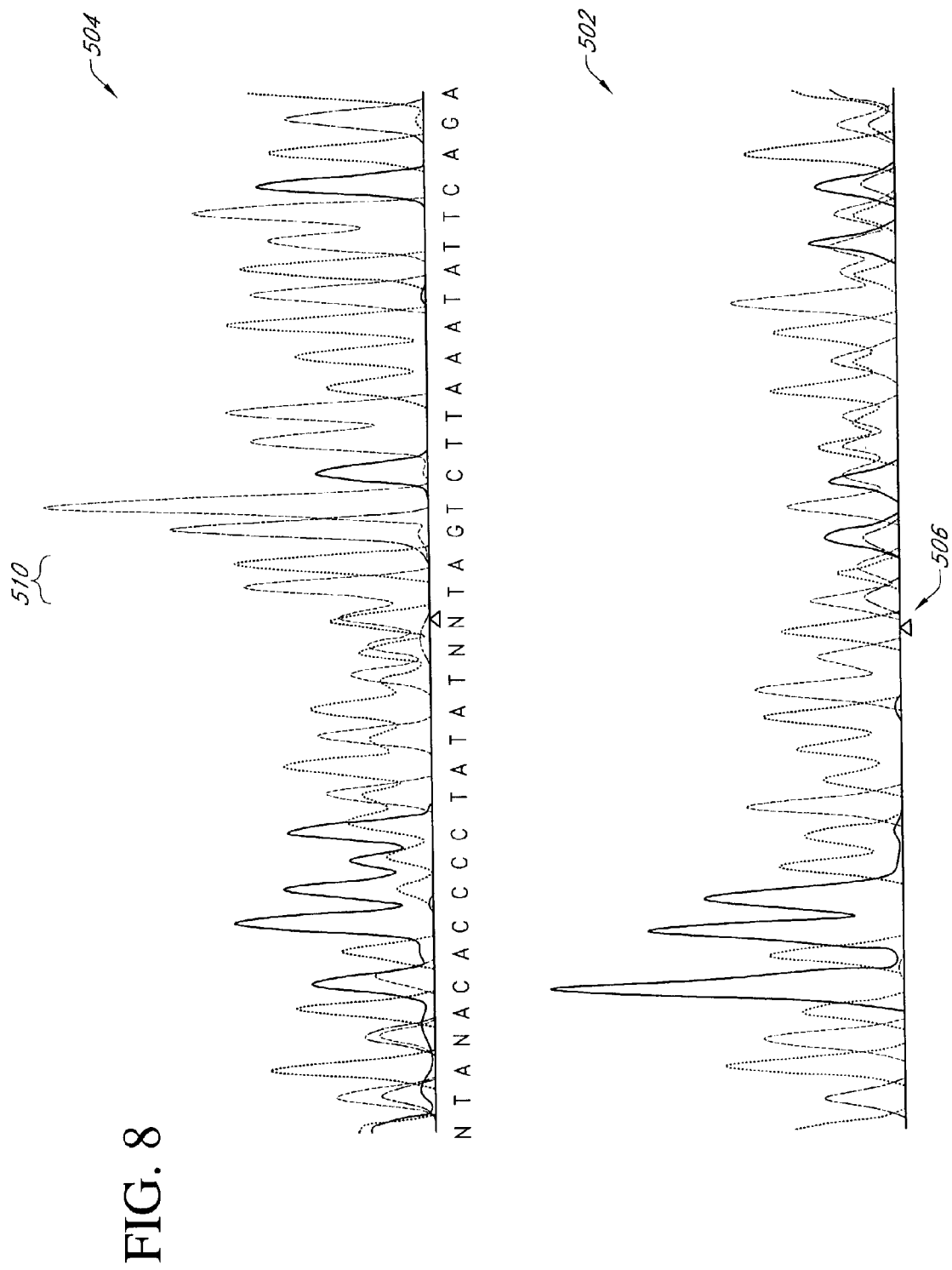
FIG. 8 illustrates a trace analysis of exemplary results obtained for a second indel mutation. (SEQ ID NO: 8)
Figure 9:
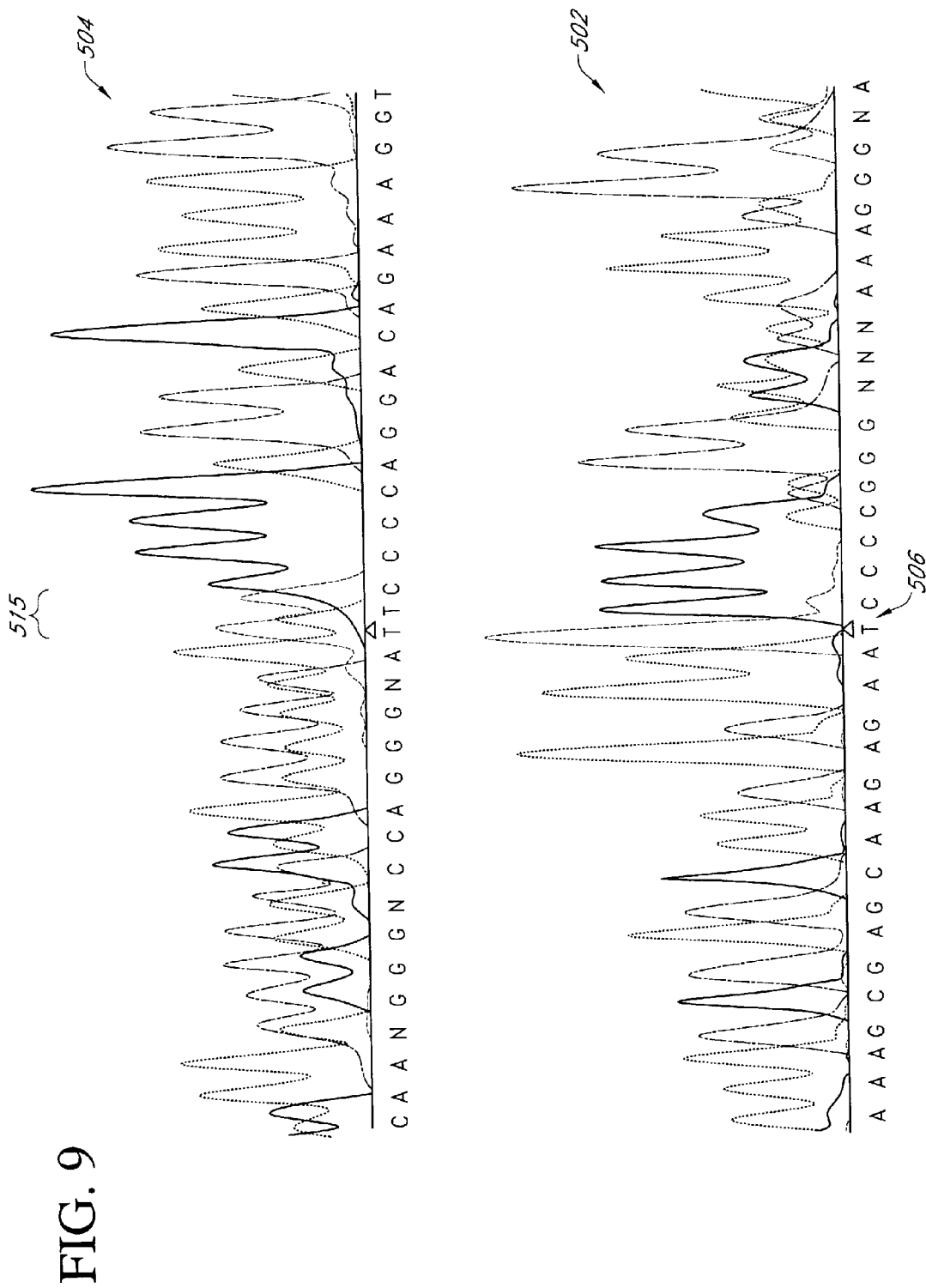
FIG. 9 illustrates a trace analysis of exemplary results obtained for a third indel mutation. (SEQ ID NO: 9) and (SEQ ID NO: 10)
Figure 10:
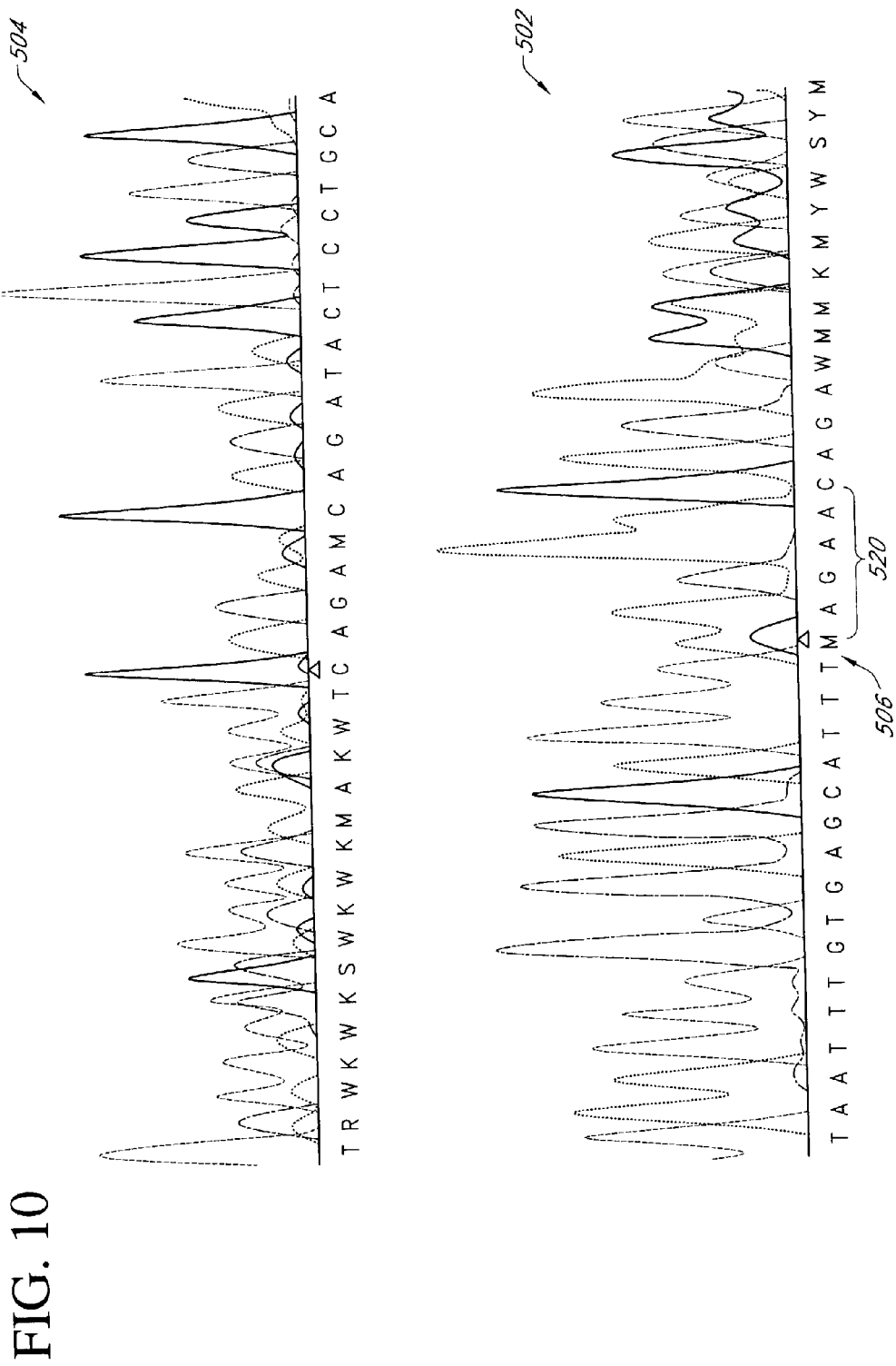
FIG. 10 illustrates a trace analysis of exemplary results obtained for a fourth indel mutation. (SEQ ID NO: 11) and (SEQ ID NO: 12)

FIGS. 8-10 illustrate exemplary traces for which the disclosed methods have been applied to predict mutational events within the target sequence. For each target sequence, a forward orientation 502 and reverse orientation 504 are shown. The centrally located indicator 506 in each trace 502, 504 further indicates the reference position from which the shift hypotheses are formed. Although, two traces 502, 504 are shown in each example, it will be appreciated that additional traces originating from either orientation may be collectively analyzed to aid in determination of the location, size, and composition of identified mutations. Furthermore, the disclosed methods may be used to distinguish multiple mutations residing in proximity to one another to desirably provide a convenient method by which to resolve regions of sequence information that would otherwise be difficult to evaluate by conventional methods.

FIG. 8 illustrates a two basepair deletion 510 comprising the base sequence "TA". As previously described the methods for mutation identification disclosed herein may aid in distinguishing mutational events based on shift hypothesis scoring. In this example the deletion is observed in the forward strand with a concomitant increase in the frequency of mixed bases to the right of the mutational event.

FIG. 9 illustrates a one basepair insertion 515 comprising the base sequence "C". In this example the insertion is observed in the reverse strand with a concomitant increase in the frequency of mixed bases to the left of the mutational event. In one aspect, the mutation identification methods may aid in distinguishing between types of mutations (e.g. insertions, deletions, and/or substitutions) by comparison of the obtained mutational event information in relation to a reference sequence. The reference sequence may further comprise expected, experimentally determined, or known sequence information for the region in which the mutational event is observed. By comparing the reference sequence information to the sequence information identified by the mutation identification methods, a determination may be made as to the type, size, orientation, and/or composition of the mutation.

FIG. 10 illustrates a five basepair insertion 520 comprising the base sequence "AAGAA". In this example the insertion is observed in the forward strand with a concomitant increase in the frequency of mixed bases to the right of the mutational event. Likewise, an concomitant increase in the frequency of mixed bases to the left of the mutational event is observed in the reverse strand.

An additional aspect of the present teachings includes an approach to estimate the certainties of the mutational analysis methods applied to a selected sequence locus thereby enhancing the quality and/or accuracy of mutational prediction and assessment. In various embodiments, estimation of certainty in this manner comprises estimating the likelihood that an observed signal is related to background noise or mixed-base presence unrelated to a mutational event. One approach that has been found to be viable in this regard provides an internal modeling of the noise in the mixed-base frequency signal. In one aspect, noise may be modeled following a Gaussian distribution while preserving an acceptable level of generality. In this case, Gaussian noise modeling may be associated with a Z-score illustrated by Equation 1:

$$\text{Equation 1:} \quad \frac{S - \mu}{\sigma}$$

In this equation, S indicates the maximum of the detection signal, $\mu$ represents the mean of the noise distribution, and $\sigma$ represents the standard deviation of the noise distribution. This concept may be applied to the shift hypothesis signal to aid in noise discrimination. Furthermore, this approach may be useful in establishing the significance of the reported results. One benefit provided by determining the probability estimate is that it may serve as an indicator to the user that the data may be amenable to reinterpretation and/or visual inspection to confirm the mutational predictions previously made. Additionally, application of a probability estimation function may aid in high-throughput cataloging without user intervention.

Figure 11:
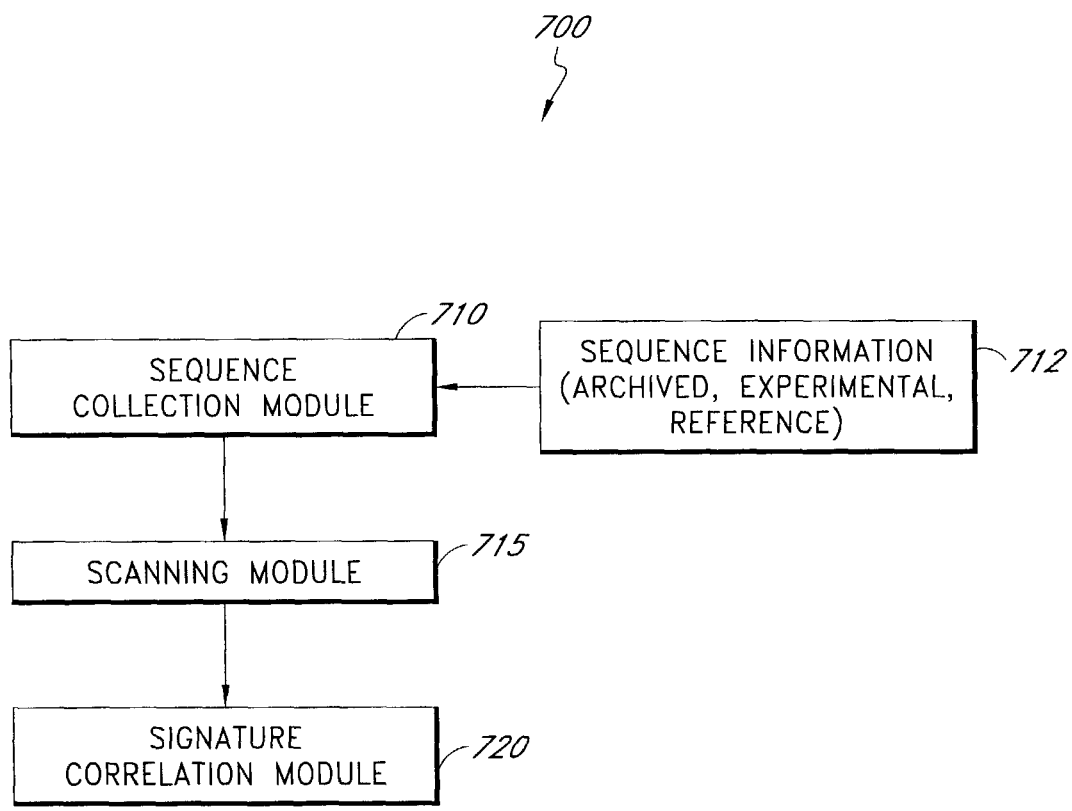
FIG. 11 illustrates a system for performing mutational analysis.

FIG. 11 illustrates an exemplary system 700 for mutational analysis that implements various functionalities of the mutation detection methods described above. In one aspect, the system for mutational analysis comprises a plurality of modules 710, 715, 720 that interoperate with one another to perform tasks associated with resolving and evaluating sequence information. It will be appreciated by one of skill in the art that these modules may be configured in a number of different ways without departing from the scope of the present invention. For example, the modules 710, 715, 720 may be combined into a single unified module, application, or hardware device that may be used to implement mutational analysis according to the present teachings. These modules may also be combined with other modules and/or applications to provide additional sequence analysis functionalities based on the data and information generated by the present system 700.

In various embodiments, a sequence collection module 710, may be used to acquire sequence information 712 to be evaluated for purposes of identifying mutations. This sequence information 712 may be obtained from numerous sources and may include for example; archived, experimental, and/or reference sequence information stored in one or more databases or information repositories. Furthermore, the sequence information 712 may be acquired directly from instrumentation to be used in rapid or high throughput analysis operations. As previously indicated, the sequence information may include trace and/or electropherogram data and may be collected in raw or processed form. Additionally, the sequence collection module 710 may provide functionality for reformatting and processing the data for presentation to the other modules in the system 700.

Following data acquisition, a scanning module 715 may be used to process the acquired sequence information. In one aspect, the scanning module 715 comprises functionality for scanning the sequence information for mixed-base signatures as described above. During mixed-base signature assessment directional or orientation dependent evaluation may be performed to identify a first mixed-base signature associated with a forward orientation of the sequence information and in a similar manner a second mixed-base signature may be identified in the reverse orientation of the sequence information. As previously described the identified first and second mixed-base signatures may be substantially reversed relative to one another and a putative mutation site may be identified at approximately an overlapping portion between the first mixed-base signature and the second mixed-base signature.

Functionality for evaluating the mixed-base signatures relative to one another to identify one or more putative mutational sites may further be contained in a signature correlation module 720. The signature correlation module 702 may also perform operations associated with characterizing the sequence occurring at the putative mutational site. In one aspect, characteristics of the mutation may be determined by comparing the mixed-base signatures and resulting sequence information to reference sequences which may be imported by the sequence collection module 710 to provide additional information on the size, composition, and other characteristics of the mutation.

It will be appreciated by one of skill in the art that other functional aspects described in association with the methods disclosed herein may be readily integrated into the system 700 for mutational analysis. As such, various systems which provide similar sequence analysis functionalities in the manners described herein are conceived to be but other embodiments of the present teachings.

The above-described teachings present novel methods by which mutational analysis and allelic differentiation may be performed. In various embodiments, use of these methods may improve the accuracy of automated systems that are designed for high-throughput sequence analysis. It is conceived that these methods may be adapted for use with numerous sequencing applications including, but not limited to, heterozygote detection, single nucleotide polymorphism analysis, and general sequence assembly and mutational analysis tasks. Additionally, these methods may be readily integrated into new and existing sequence processing applications, software, and instrumentation.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

APPENDIX A

```
function mb2 = mixedBaseMatrix( asmFigObj )
%
%   mb2 = mixedBaseMatrix( asmFigObj )
%
%   returns signal indicating where ( if any ) a heterozygous frameshift has
%   been detected
%
%   History
%           1.01            JMS
%                           Creation.
%           10.03.01        JMS
%                           Revisited to start establishing feasibility. Added comments
%
% mixed_ratio = 10.0;
% style = 'loose';
%asmFigObj = callMixed( asmFigObj, mixed_ratio, style );
asm = asmFigObj.asm;
mb1 = zeros( asm.num_lanes, asm.num_bases );
mb2 = zeros( asm.num_lanes, asm.num_bases );
num_f = zeros( 1, asm.num_bases );
num_r = num_f;
for i=1:asm.num_lanes
    for j=1:asm.lanes(i) .num_strands
        start = asm.lanes(i) .starts(j);
        stop = asm.lanes(i) .stops(j);
        if asm.lanes(i) .orientations(j) == 'f'
            mb1(i, :) = mb1(i, :) + ismember ( asm.lanes(i) .alignments(j), ...
                'RYMKSW' ) + 2*ismember ( asm.lanes(i) .alignments(j), ...
                'HVBD' );
            num_f( start:stop ) = num_f( start:stop ) + 1;
        else
            mb2(i, :) = mb2(i, :) - (ismember ( asm.lanes(i) .alignments{j}, ...
                'RYMKSW' ) + 2*ismember ( asm.lanes(i) .alignments{j}, ...
                'HVBD' ) );
```

APPENDIX A-continued

```
            num_r ( start:stop ) = num_r ( start:stop ) + 1;
        end
    end
end
num_f ( find( num_f == 0.0 ) ) = 1;
num_r ( find( num_r == 0.0 ) ) = 1;
%   Compute average # of mixed bases for each column for each orientation
mb( 1, : ) = sum( mb1 ) ./ num_f;
mb( 2, : ) = sum( mb2 ) ./ num_r;
%   Parameter for window over which signal is detected
window = 28;
% Controls tightness of −1:1 step function filter
epsilon1 = 10;
%   Construct gaussian for detecting signal
%   and separate gaussian for smoothing final answer
d = [ −1*ones( 1, window ) 1 ones( 1, window ) ];
x = (0:2*window) − window;
e1 = exp( -x.'/ ( epsilon1*window*window ) );
e1 = e1 / sum(e1);
e2 = exp( -x. '/ ( 1.0 * window * window ) );
e2 = e2 / sum(e2);
d = d .* e1;
%   In one fell swoop, detect signal and smooth it
mb2 = conv( abs( conv( d, sum( mb ) ) ), e2 );
%   Convolution appends undesirable beginning and end points
mb2( 1: length(e1) ) = [ ];         % trim off beginning
mb2( end − 2*window : end ) = [ ];  % trim off end
```

APPENDIX B

```
function [ pos, shift, shiftHypotheses ] = findHeteroFrameshiftMutation( asmFigObj )
%
%       [ pos, shift, shiftHypotheses ] = findHeteroFrameshiftMutation( asmFigObj )
%
%       Returns predicted position and shift for a heterozygous frameshift mutation
%       Also returns vote for each shift hypothesis.
%
%       History
%       10.30.01    JMS
%                   Start of implementation for algorithm which identifies nature
%                   of shift in heterozygous frameshift mutations
MAX_FRAMESHIFT = 30;            % governs largest frameshift searched for
MAX_DETECTION_WINDOW = 45;      % governs how far shift is looked for
MAX_SCAN_FOR_MIXED = 7;         % how far from the detected position to look for the first mixed base
%       Detect location of heterozygous frameshift mutation
detectionSignal = mixedBaseMatrix( asmFigObj );
%       For right now, just use the maximum of the detection signal for the
%       detected position. Can get much more sophisticated later.
[ maxSignal, pos ] = max( detectionSignal );
asm = asmFigObj.asm;
shift = 0;
fwdIndex = pos;
revIndex = pos;
%       Scan to the right for the first mixed base in the forward orientation
%       Scan to the left for the first mixed base in the reverse orientation
foundFwd = 0;
foundRev = 0;
for i=1:asm.num_lanes
    for j=1:asm.lanes(i) .num_strands
        % Check that the column position is contained in the strand being searched
        if asm.lanes(i) .starts(j) <= pos & asm.lanes(i) .stops(j) >= pos
            if ~foundFwd & asm.lanes(i) .orientations(j) == 'f'
                numScanned = 0;
                while ~isMixed( asm.lanes(i) .alignments(j) ( fwdIndex ) ) & numScanned < MAX_SCAN_FOR_MIXED
                    fwdIndex = fwdIndex + 1;
                    numScanned = numScanned + 1;
                end
                if numScanned < MAX_SCAN_FOR_MIXED
                    foundFwd = 1;
                else
                    fwdIndex = pos;
                end
            end
            if ~foundRev & asm. lanes(i) .orientations(j) == 'r'
                numScanned = 0;
                while ~isMixed( asm. lanes(i) .alignments(j) ( revIndex ) ) & numScanned < MAX_SCAN_FOR_MIXED
                    revIndex = revIndex − 1;
```

APPENDIX B-continued

```
            numScanned = numScanned + 1;
          end
          if numScanned < MAX_SCAN_FOR_MIXED
            foundRev = 1;
          else
            revIndex = pos;
          end
        end
      end
    end
  end
end
if ~foundFwd | ~foundRev
  warning( 'Couldn' 't find files in both orientations :(');
  return;
end
%      Proceed incrementally, evaluating each frameshift hypothesis
shiftHypotheses = zeros( 1, MAX_FRAMESHIFT );
for i = 1:MAX_DETECTION_WINDOW
  for j=1:asm. num_lanes
    for k=1:asm. lanes(j). num_strands
      for l=1:MAX_FRAMESHIFT
        skipHypothesis = 0;                                 % whether to skip this comparison because at end of read
        if asm.lanes( j ) .orientations( k ) == 'f'
          if fwdIndex + 1 > asm. lanes( j ) .stops( k ) | fwdIndex < asm. lanes(j) .starts(k)
            skipHypothesis = 1;
          else
            currentBase = asm. lanes( j ) .alignments { k }( fwdIndex );
            shiftedBase = asm.lanes( j ) .alignments { k } ( fwdIndex + 1 );
          end
        else
          if revIndex – 1 < asm. lanes( j ) .starts( k ) | revIndex > asm. lanes(j) .stops(k)
            skipHypothesis = 1;
          else
            currentBase = asm. lanes( j ) .alignments{ k } ( revIndex );
            shiftedBase = asm. lanes( j ) .alignments{ k } ( revIndex – 1 );
          end
        end
        if ~skipHypothesis
          if mixedBaseIntersect( currentBase, shiftedBase )
            shiftHypotheses( 1, 1 ) = shiftHypotheses( 1, 1 ) + 1;
          else
            shiftHypotheses( 1, 1 ) = shiftHypotheses( 1, 1) – 2;
          end
        end
      end
    end
  end
  fwdIndex = fwdIndex + 1;
  revIndex = revindex –1;
end
[ shiftSignal, shift ] = max( shiftHypotheses );
%===============================================================
%
% Returns 1 if c is in [ RYKMSWHVBDN ]
%
function mixed = isMixed( c )
mixed = ismember ( c, 'RYKMSWHVBDN' );
%===============================================================
%
% Returns 1 if IUB bases a and b share a base in common
%
function inter = mixedBaseIntersect( a, b )
aBits = baseBinary( a );
bBits = baseBinary( b );
inter = bitand( aBits, bBits ) > 0;
```

What is claimed is:

1. A method for identifying a putative mutation site within a target sequence of a sample comprising two or more discrete sequences, the method comprising:
   providing a mutational analysis module;
   collecting sequence information for the target sequence, comprising forward and reverse orientation sequence information, the forward orientation sequence information corresponding to a forward orientation sequence, and the reverse orientation sequence information corresponding to a reverse orientation sequence;
   scanning the forward orientation sequence information for a first mixed-base signature and the reverse orientation sequence information for a second mixed-base signature wherein the mixed-base signatures are derived from a selected locality of the target sequence;
   comparing the first mixed-based signature relative to the second mixed-base signature to generate a comparison;
   identifying a putative mutation site based on the comparison of the first mixed-base signature and the second mixed-base signature; and
   displaying the putative mutation site to a user,
   wherein the mutational analysis module comprises a hardware device and performs at least one of the comparing and the identifying.

2. The method of claim 1, wherein the first and the second mixed-base signatures comprise a pure-base region having a first frequency of mixed-bases followed by a mixed-base region having a second frequency of mixed-bases higher than the first frequency.

3. The method of claim 2, wherein the pure-base region and the mixed-base region of the first mixed-base signature are oppositely oriented relative to the pure-base region and the mixed-base region of the second mixed-base signature.

4. The method of claim 1, wherein scanning the forward orientation for a first mixed-base signature and the reverse orientation for a second mixed-base signature further comprises:
performing a pattern detection operation to assess mixed-base stretches in the forward and reverse orientation sequence information; and
associating the putative mutation site with a location within the target sequence wherein mixed-base stretches in the forward and reverse orientation sequences are oppositely aligned.

5. The method of claim 4, wherein the pattern detection operation further comprises:
performing a Gaussian smoothing operation and convolution assessment on the forward and reverse orientation sequence information.

6. The method of claim 1, further comprising:
identifying an indel mutation having a characteristic size which is associated. with the putative mutation site by forming a plurality of shift hypotheses corresponding to predicted sizes for the indel mutation that are resolved by performing a plurality of indel searches using the forward and reverse orientation sequence information to identify one or more shift hypotheses that are supported by the first or the second mixed-base signatures.

7. The method of claim 6, wherein at least one of the shift hypotheses comprises a putative insertion having a selected size such that when inserted into the putative mutation site results in a sequence signature that is supported by the first or the second mixed-base signatures.

8. The method of claim 7, wherein the selected size for the putative insertion is between approximately one and fifty basepairs in length.

9. The method of claim 6, wherein at least one of the shift hypotheses comprises a putative deletion having a selected size such that when deleted from the putative mutation site results in a sequencing signature that is supported by the first or the second mixed-base signatures.

10. The method of claim 9, wherein the selected size for the putative deletion is between approximately one and fifty basepairs in length.

11. The method of claim 6, wherein each shift hypothesis is associated with a value indicative of the relative degree of support indicated by the first or the second mixed-base signatures.

12. The method of claim 11, wherein the value associated with each shift hypothesis is representative of a relative goodness of fit with the first or the second mixed-base signatures.

13. The method of claim 11, wherein the value associated with each shift hypothesis is determined by incrementing the value for basecalls within the mixed-base signature that support the shift hypothesis and decrementing the value for basecalls within the mixed-base signature that do not support the shift hypothesis.

14. The method of claim 11, wherein the indel mutation is associated with the shift hypothesis having the greatest total value.

15. The method of claim 6, wherein the indel searches are performed starting with the putative mutation site to between approximately 20 and 100 basepairs downstream of the putative mutation site.

16. The method of claim 6, further comprising:
identifying the sequence of the indel mutation by evaluating a composition of the first mixed-base signature associated with the forward orientation sequence information and a composition of the second mixed-base signature associated with the reverse orientation sequence information.

17. The method of claim 16, wherein the sequence of the indel mutation is further identified by assessing the mixed-bases of each mixed-base signature to discriminate between sequence information associated with a sequence fragment containing the indel mutation and a sequence fragment lacking the indel mutation.

18. The method of claim 17, wherein indel mutation sequence determination provides a means to perform allelic differentiation.

19. A method for performing allelic differentiation, the method comprising:
providing a mutational analysis module;
collecting sequence information for a selected target sequence locus;
identifying a putative mutational event located within the selected target sequence locus by scanning the sequence information for a mixed-base signature;
identifying the size of the putative mutational event by forming a plurality of shift hypotheses corresponding to predicted sizes for the putative mutational event that are resolved by performing a plurality of indel searches using the sequence information to identify one or more shift hypotheses that are supported by the mixed-base signature; and
displaying the putative mutational event to a user,
wherein the mutational analysis module comprises a hardware device and the identifying a putative mutational event and identifying the size of the putative mutational event are performed by the mutational analysis module.

20. The method of claim 19, wherein the mixed-base signature comprises a region of sequence information having a first frequency of mixed-bases followed by a region of the sequence information having a second frequency of mixed-bases higher than the first frequency.

21. The method of claim 20, wherein the sequence information comprises forward and reverse orientation sequence information.

22. The method of claim 21, wherein the mixed-base signature further comprises:
a first region of sequence information in the forward orientation sequence information having a third frequency of mixed-bases followed by a fourth frequency of mixed-bases higher than the third frequency; and
a second region of sequence information in the reverse orientation sequence information having a fifth frequency of mixed-bases followed by a sixth frequency of mixed-bases higher than the fifth frequency.

23. The method of claim 22, wherein the first region and the second region are oppositely aligned with respect to one another in reference to the target sequence locus.

24. The method of claim 23, wherein the putative mutation event is further identified by:
identifying a first transition point between the third frequency of mixed bases and the fourth frequency of mixed-bases in the first region;
identifying a second transition point between the fifth frequency of mixed bases and the sixth frequency of mixed bases in the second region;
comparing the first and the second transition points to identify a location within the selected target sequence locus that corresponds to the first and second transition points; and
associating the putative mutation event with the location corresponding to the first and second transition points.

25. The method of claim 24, wherein the first and the second transition points are identified by performing a pattern detection operation that assesses mixed-base frequencies.

26. The method of claim 25, wherein the pattern detection operation further comprises:
performing a Gaussian smoothing operation and convolution assessment on the first region of sequence information in the forward orientation sequence information and second region of sequence information in the reverse orientation sequence information.

27. The method of claim 19, wherein at least one of the plurality of shift hypotheses corresponds to a putative insertion.

28. The method of claim 19, wherein at east one of the plurality of shift hypotheses corresponds to a putative deletion.

29. The method of claim 19, wherein resolving the plurality of indel searches further comprises:
performing indel searches starting at approximately the first mixed-base adjacent to the location of the putative mutation event wherein, for each shift hypothesis, basecalls located in the sequence information that are positioned at a distance approximate equivalent to the size of the shift hypothesis are evaluated to determine the relative degree of support for the shift hypothesis.

30. The method of claim 29, wherein the relative degree of support for the shift hypothesis corresponds to a goodness of fit between the shift hypothesis and the mixed-base signature.

31. The method of claim 29, wherein each shift hypothesis is associated with a value indicative of the relative degree of support for the shift hypothesis.

32. The method of claim 31, wherein the value associated with each shift hypothesis is determined by incrementing the value for basecalls within the mixed-base signature that support the shift hypothesis and decrementing the value for basecalls within the mixed-base signature that do not support the shift hypothesis.

33. The method of claim 31, wherein the putative mutational event is associated with the shift hypothesis having the greatest value.

34. The method of claim 19, further comprising:
identifying the sequence of each putative mutational event by evaluating a composition of mixed-bases associated with the one or more supported shift hypotheses.

35. A mutational analysis system comprising:
a sequence collection module that receives sequence information for a target sequence, comprising forward and reverse orientation sequence information;
a scanning module that scans the sequence information to identify a first mixed-base signature associated with the forward orientation sequence information and a second mixed-base signature associated with the reverse orientation sequence information;
a signature correlation module that evaluates the first mixed-base signature relative to the second mixed-base signature to identify one or more putative mutation sites; and
a display configured to display the one or more putative mutation sites to a user,
wherein the scanning module comprises a hardware device.

36. The system of claim 35, wherein the first and the second mixed-base signatures comprise a pure-base region having a first frequency of mixed-bases followed by a mixed-base region having a second frequency of mixed-bases higher than the first frequency.

37. The system of claim 36, wherein the pure-base region and the mixed-base region of the first mixed-base signature are oppositely oriented relative to the pure-base region and the mixed-base region of the second mixed-base signature.

38. The system of claim 35, wherein the scanning module identifies the mixed-base signatures by performing a pattern detection operation to assess mixed-base stretches in the forward and reverse orientations and. the signature correlation module identifies the putative mutation sites at a transition region wherein the mixed-base stretches in the forward and reverse orientations are substantially oppositely aligned.

39. The system of claim 35, wherein the signature correlation module further. identifies an indel mutation having an associated size located in proximity to the putative mutation site by forming a plurality of shift hypotheses corresponding to predicted sizes for the indel mutation that are resolved by performing a plurality of indel searches using the forward and reverse orientation sequence information to identify one or more shift hypotheses that are supported by the first or the second mixed-base signatures.

40. The system of claim 35, wherein identification of the one or more putative mutation sites by the signature correlation module provides a means to identify allelic differences within the sequence information.

41. The system of claim 35, wherein the signature correlation module further provides a means to identify the type of mutation associated with the putative mutational site.

42. The system of claim 35, wherein the type of mutation is selected from the group consisting of: insertions, deletions, and substitutions.

43. A method for mutational analysis comprising:
providing a mutational analysis module;
receiving sequence information for a target sequence, comprising forward and reverse orientation sequence information;
scanning the sequence information to identify a first mixed-base signature associated with the forward orientation sequence information and a second mixed-base signature associated with the reverse orientation sequence information;
evaluating the first mixed-base signature relative to the second mixed-base signature to identify one or more putative mutation sites; and
displaying the one or more putative mutation sites to a user,
wherein the mutational analysis module comprises a hardware device and the scanning and evaluating are performed by the mutational analysis module.

44. The method of claim 43, wherein the first mixed-base signature comprises a pure-base region having a first frequency of mixed-bases followed by a mixed-base region having a second frequency of mixed-bases higher than the first frequency and, wherein the second mixed-based signature comprises a pure-base region having a third frequency of mixed-bases followed by a mixed-base region having a fourth frequency of mixed-bases higher than the third frequency.

45. The method of claim 44, wherein the pure-base region and the mixed-base region of the first mixed-base signature are oppositely oriented relative to the pure-base region and the mixed-base region of the second mixed-base signature.

46. The method of claim 45, wherein the one or more putative mutation sites are identified within the at least one transition region between the pure-base region and the mixed-base region for the first and second mixed-base signatures.

47. The method of claim 43, wherein the mixed-base signatures are identified by performing a pattern detection operation to assess mixed-base stretches in the forward and reverse orientations and the signature correlation module identifies the putative mutation sites at a transition region wherein the mixed-base stretches in the forward and reverse orientations are oppositely aligned.

48. The method of claim 43, wherein an indel mutation having an associated size is identified in proximity to the putative mutation site by forming a plurality of shift hypotheses corresponding to predicted sizes for the indel mutation that are resolved by performing a plurality of indel searches using the forward and reverse orientation sequence information to identify one or more shift hypotheses that are supported by the first or the second mixed signatures.

49. The method of claim 43, wherein identification of the one or more putative mutation sites provides a means to identify allelic differences within the sequence information.

* * * * *